United States Patent
Seex et al.

(10) Patent No.: US 11,504,106 B2
(45) Date of Patent: Nov. 22, 2022

(54) CLAMPING RETRACTOR ASSEMBLY

(71) Applicant: Retrospine Pty Ltd., Kingswood (AU)

(72) Inventors: Kevin Seex, Kingswood (AU); Donald Fry, Kingswood (AU)

(73) Assignee: RETROSPINE PTY LTD, Kingswood (AU)

(*) Notice: Subject to any disclaimer, the term of this patent is extended or adjusted under 35 U.S.C. 154(b) by 192 days.

(21) Appl. No.: 16/521,220

(22) Filed: Jul. 24, 2019

(65) Prior Publication Data
US 2020/0390431 A1 Dec. 17, 2020

Related U.S. Application Data

(63) Continuation of application No. 13/901,070, filed on May 23, 2013, now abandoned.

(30) Foreign Application Priority Data

May 28, 2012 (AU) .................. 2012902187

(51) Int. Cl.
| | |
|---|---|
| *A61B 17/02* | (2006.01) |
| *A61B 17/08* | (2006.01) |
| *A61B 17/34* | (2006.01) |
| *A61B 90/00* | (2016.01) |
| *A61B 17/00* | (2006.01) |

(52) U.S. Cl.
CPC .............. *A61B 17/02* (2013.01); *A61B 17/08* (2013.01); *A61B 17/3403* (2013.01); *A61B 90/06* (2016.02); *A61B 2017/00349* (2013.01); *A61B 2017/00407* (2013.01); *A61B 2017/00862* (2013.01); *A61B 2017/00991* (2013.01); *A61B 2017/3405* (2013.01); *A61B 2017/3492* (2013.01); *A61B 2090/062* (2016.02)

(58) Field of Classification Search
CPC ...... A61B 17/02; A61B 17/0206; A61B 17/08
See application file for complete search history.

(56) References Cited

U.S. PATENT DOCUMENTS

| | | | | |
|---|---|---|---|---|
| 3,749,088 A | * | 7/1973 | Kohlmann | A61B 17/0293 600/215 |
| 4,852,552 A | * | 8/1989 | Chaux | A61B 17/0206 600/232 |
| 5,512,038 A | * | 4/1996 | O'Neal | A61B 17/0206 600/210 |

* cited by examiner

*Primary Examiner* — Si Ming Ku
(74) *Attorney, Agent, or Firm* — B. Aron Schulman; Stites & Harbison PLLC

(57) ABSTRACT

An assembly for retracting soft tissue in a surgical incision is provided, the assembly including a supporting member having first and second ends; a retractor blade having a first distal end and a second proximal end retained at the first end of the support member; a retaining arm which co-operates with the support member and receives and supports a clamping assembly; and an adjusting assembly which engages the support member and allows the clamping assembly to advance and retract relative to the retractor blade.

15 Claims, 12 Drawing Sheets

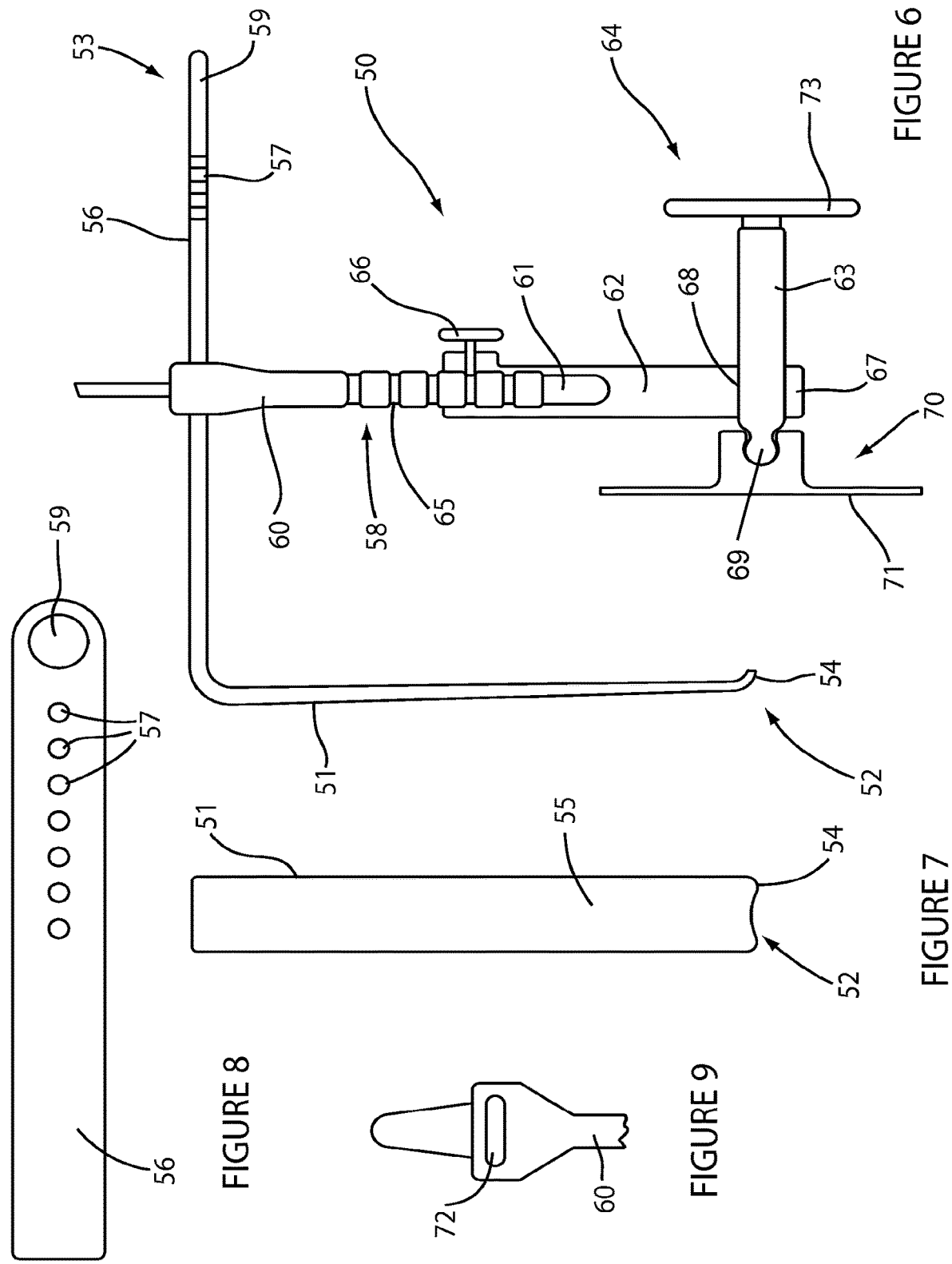

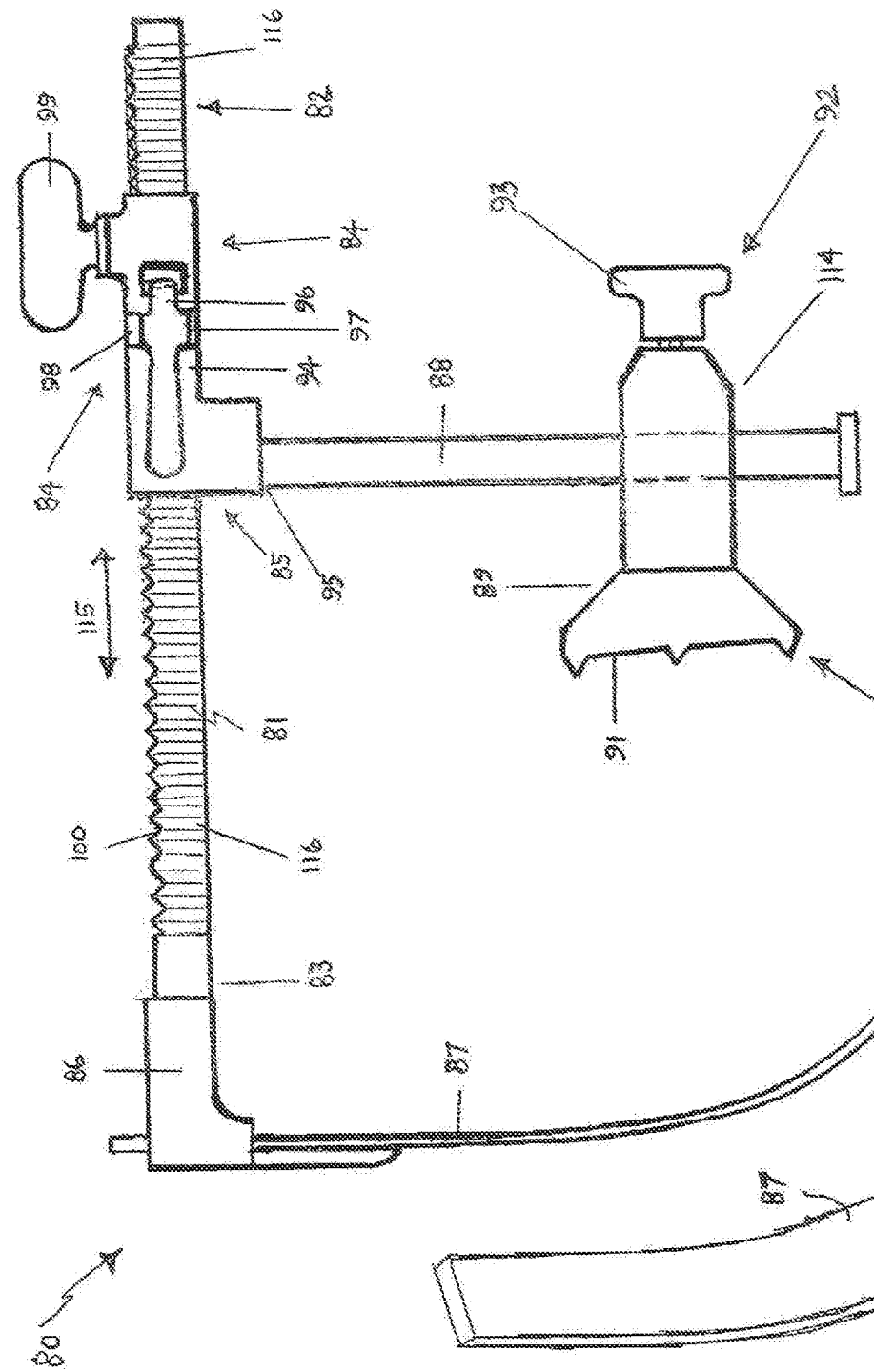

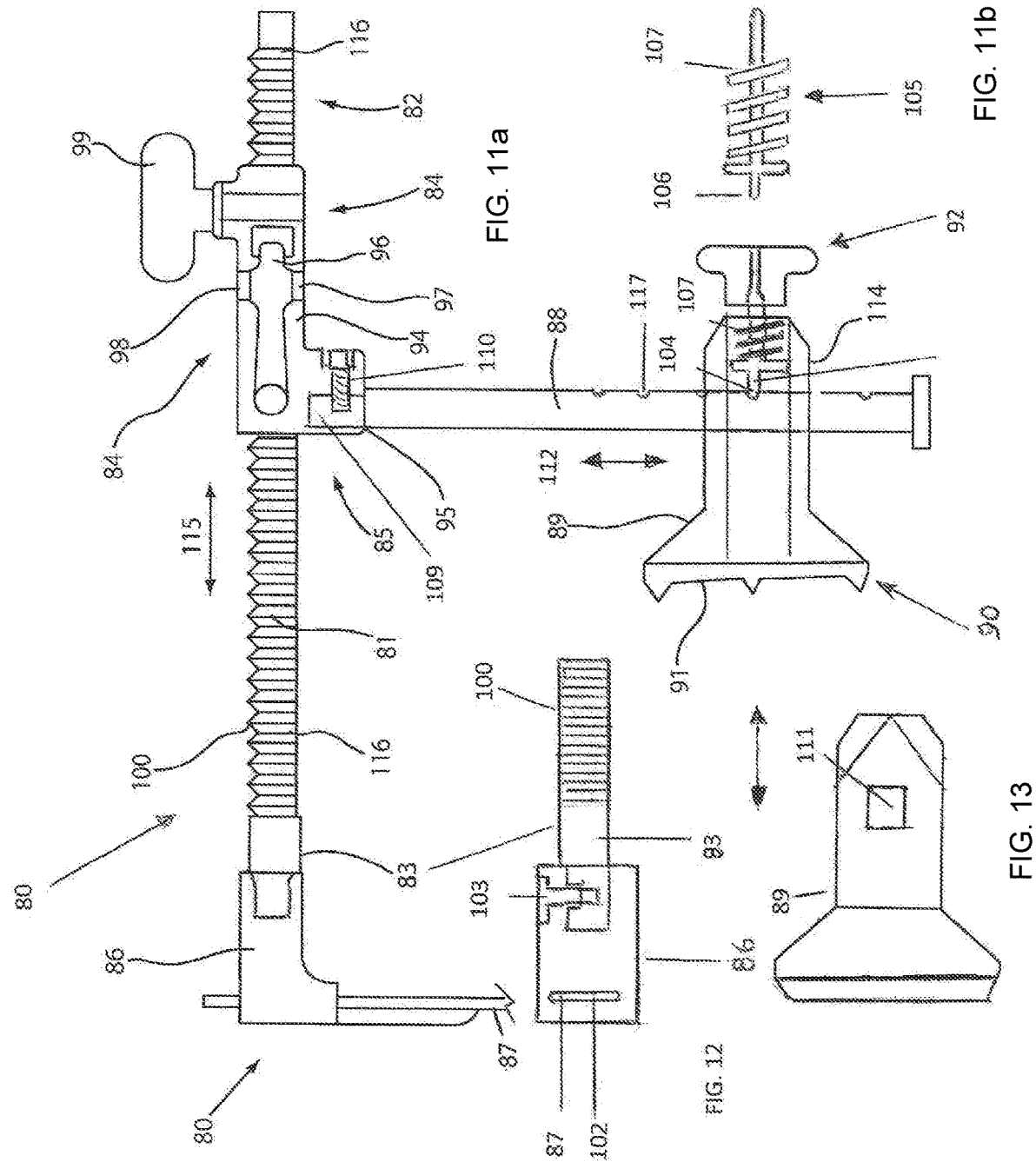

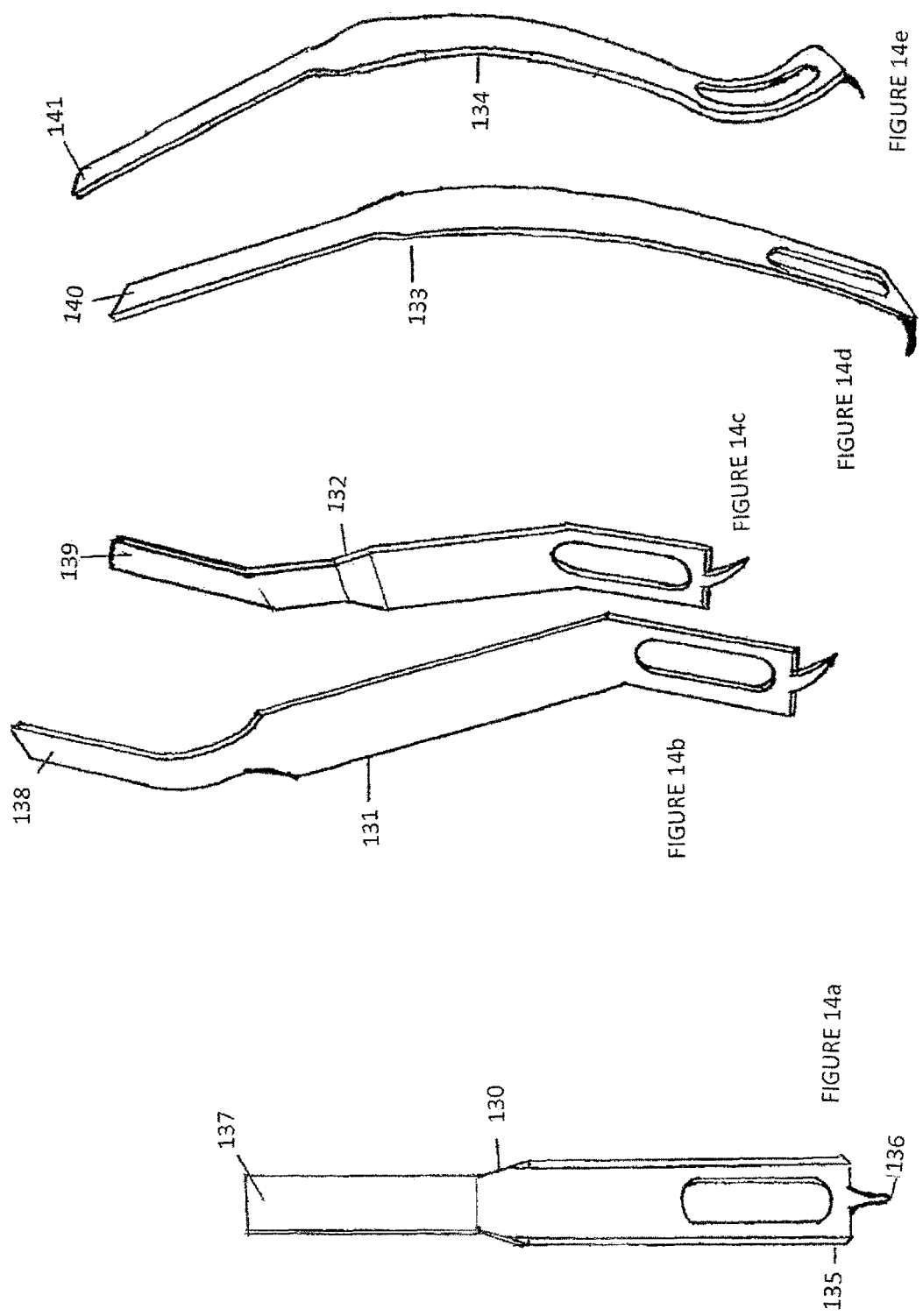

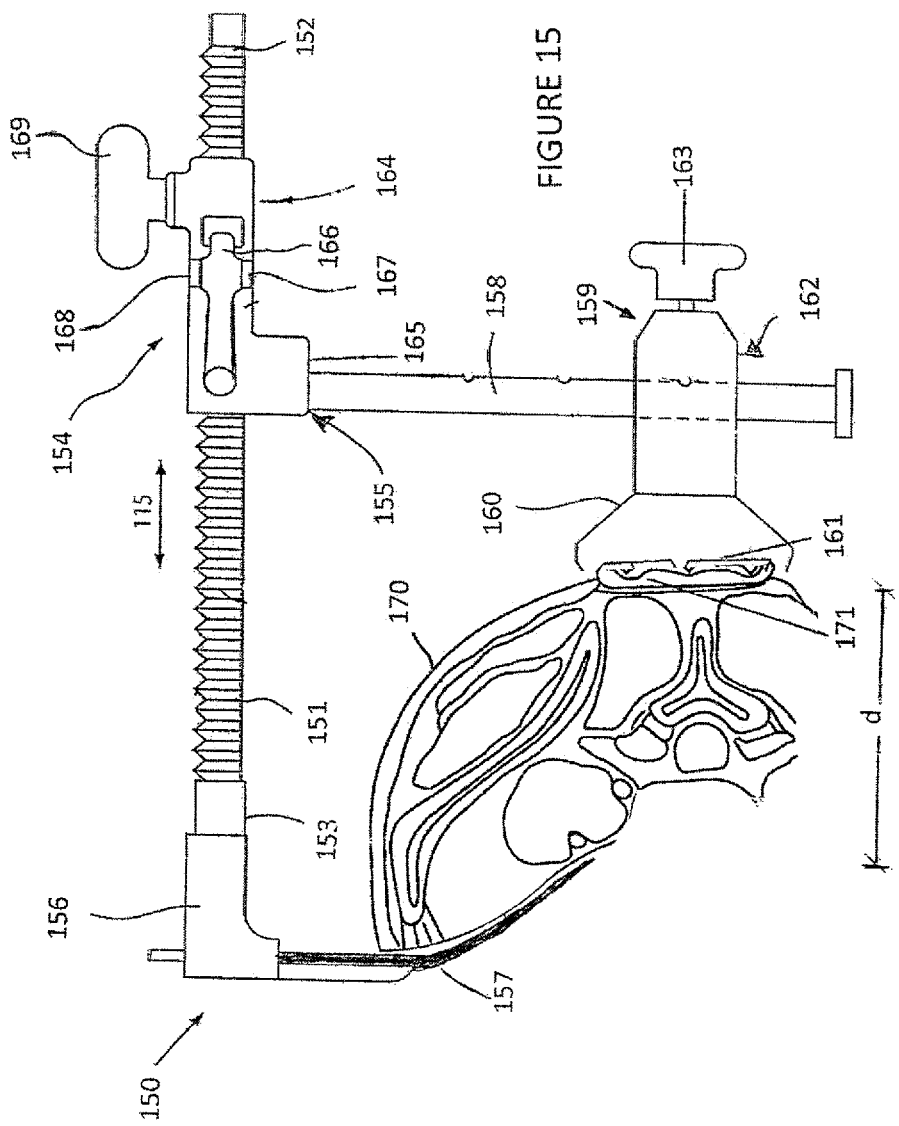

CLAMPING RETRACTOR ASSEMBLY

CROSS-REFERENCE TO RELATED APPLICATIONS

This application is a continuation application of U.S. Ser. No. 13/901,070, filed May 23, 2013, which claimed the benefit of Australian patent application 2012902187, filed May 28, 2012, all of said applications incorporated herein by reference.

BACKGROUND

The present invention relates to retraction assemblies and more particularly relates to assemblies for retracting soft tissue during surgery and particularly during spinal surgery. The invention further relates to a G clamp retractor which has an internal component which engages a wound to retract soft tissue and an external component which has the capacity to set and control the degree of retraction. The invention further relates to an assembly which more efficiently retracts the psoas muscle to allow access to spinal vertebrae.

PRIOR ART

In the field of surgery, conventional retractors used in applications such as spinal surgery include a retractor blade portion that is in contact with the soft tissues and a handle portion that controls the blade position. The blades are inserted into position through the surgical wound. The direction of force applied by the blades to keep the wound open is usually at right angles to this line of entry. This creates mechanical disadvantage and complex mechanisms may need to be employed to overcome tissue resistance— i.e. the tendency or bias of a wound towards closure. As most retractors operate from the wound surface, the distance from the wound surface to the point of contact between retractor blades and the tissue works similar to a vertical cantilever which is suboptimal for the surgeon's requirement for access to the site and also a free end cantilever is not ideal as there is significant force applied at the free end of the retractor by soft tissue. A short retractor handle is generally easier to control and apply force with as the moment is lower. In a long blade the moment is higher. This is especially true when handle is roughly parallel with blade. Strong mechanisms are sometimes required, strong materials needed. Also the known mechanisms occupy space restricting the surgeons access and they may also be complex. The stability of the retractor may also be a problem. Some dual or multi bladed retractors apply spreading forces against the wound edges to stabilize retractors but these apply force that may potentially injure tissues unnecessary for the purpose of exposure but in order to gain retractor stability. Stability is desirable but tissue injury is not. An alternative solution is to use table mounted mechanisms with long mechanical arms but these have great mechanical inefficiency because of the distance from point of fixation i.e. the table, to the point of at which retraction pressure is applied distally. This problem of the difficulty in applying force and retractor instability is worse the deeper the wound and especially when deep structures require retraction.

Spinal operations for various conditions commonly require deep wounds especially when the approach is lateral, anterior lateral or anterior to the spine. Retracting the psoas muscle posteriorly to expose the lateral or anteriolateral spine can be problematic because of the size of the muscle and the depth of the wound. At L45 from a lateral approach this is made even harder because the iliac crest commonly impedes true lateral access for the retractors and instruments, meaning an oblique approach to the spinal disc may be required.

In many spinal operations the retractors lack stability e.g. with deep multi bladed retractors and various forms of tubular retractors. Such retractors regularly require table fixed adjustable arms to improve the stability for the retractor.

Conventional retractors work directly through the surgical wound. Retractors are known that are employed in endoscopic surgery which enter the abdominal cavity via separate ports or incisions. These work directly and do not connect with other parts of a retractor system. There is a system described in the paper by Rao modified from Nakamura. (J Neurosurg Spine 5: 468-470, 2006 entitled "*Dynamic retraction of the psoas muscle to expose the lumbar spine using the retroperitoneal approach*"

Technical Note

GANESH RAO, M.D., ROBERT BOHINSKI, M.D., PH.D., IMAN FEIZ-ERFAN, M.D., AND LAURENCE D. RHINES, M.D.
Nakamura H, Ishikawa T, Konishi S, Seki M, Yamano Y: Psoas strapping technique: a new technique for laparoscopic anterior lumbar interbody fusion. J Am Coll Surg 191: 686-688, 2000)

That paper describes a technique which applies retraction force via a thread through the patient body wall. A conventional approach is used for the main operation. Tissues are retracted by passing thread through the psoas muscle on a needle. The needle is then removed from thread. A hollow needle is passed through the body wall. Both ends of the thread are then passed through the hollow needle outside the skin. Threads are pulled to gain psoas retraction and then anchored with a forceps which is pulled back by the muscle force against the skin. This system provides for efficient application of retraction force by line of pull being as close as possible to the desired direction of retraction and by avoiding a cantilevered handle. It would be advantageous if retraction was applied to the psoas muscle by a blade rather than by a thread as blades retract muscle smoothly and are less injurious to surface nerves than the potential strangulation effect from a thread. Blades can also be selected to fit the anatomy under retraction. The blind needle passage may also damage nerves within the psoas muscle. Threading a needle in a wound is fiddly, threads passing through retractor tissues have less stability than a handle. Threads passed through a muscle cannot be repositioned easily.

It would be an advantage in such operations to have a method of retracting the psoas muscle posteriorly to expose the spine or the disc space that avoids the force application and distribution problems associated with deep wounds, long handles and oblique access. These known surgical retraction methods currently all lead to retractors working at considerable mechanical disadvantage.

It would be an advantage to reduce or eliminate the mechanical disadvantage occasioned by the known retraction devices and assemblies and to improve retractor stability and to avoid the aforesaid problems.

The present applicant has previously described devices to improve mechanical advantage for retraction using bone fixation combined with mechanisms to allow retractor blade rotation.

INVENTION

The present invention provides an assembly which more efficiently retracts muscle to allow access to spinal vertebrae. The present invention further provides an assembly which more efficiently retracts the psoas muscle to allow access to spinal vertebrae. The present invention also provides a method of retraction of soft tissues during spinal surgery which ameliorates the problems of the prior art assemblies and methods.

According to one embodiment a retractor blade and handle are inserted through a main wound. A second handle is inserted through a separate incision. Blade and second handle are then connected in the main wound. Pulling the second handle retracts the blade and tissues efficiently in a preferred direction. The assembly described herein allows the maintenance of the required amount of retraction and maintenance of the retractor position and without either manual holding or securing of the retractor handle to a table mounted arm. Passage of the second handle through the body wall limits motion except for motion in line with the handle. Limiting the motion of the retractor handle further is achieved by its relationship with a plate. The plate is in contact with the body wall. Internally the muscle under retraction exerts a pull on the retractor and its handle. Internal movement of the handle is however prevented by an adjustable stop on the handle which is forced against the plate by the retractor pull. Retraction can be adjusted by movement of the stop.

In its broadest form the present invention comprises:
an assembly for retracting soft tissue in a surgical wound, the assembly comprising;
a retractor blade having a first distal end and a second end which includes an associated support member,
a retaining member having a distal end which engages the support member and a second proximal end which includes a hand operable clamping assembly;
an adjustable stop which engages a plate, wherein the plate engages a skin surface of a patient to resist said retraction by the soft tissue as the support member is urged to induce retraction by the blade.

According to a preferred embodiment, the support member includes a formation which co operates with a guide member. Preferably the formation is an opening which receives an end of the guide member. According to one embodiment the retaining arm includes at least one threaded region which co operates with said plate, adjustable stop and a locking nut. The guide member co operates with the support member to enable setting of a retraction condition. The assembly allows adjustment of retraction by increasing or decreasing a retraction force.

In another broad form the present invention comprises:
an assembly for retracting soft tissue in a surgical wound, the assembly comprising;
a retractor blade having a first distal end and a second end which engages an associated detachable first handle,
a second handle having a first distal end which engages said blade and a second proximal end which includes a hand operable control element and intermediate therebetween an adjustable stop which engages a plate,
a guide which engages a second end of the first handle to facilitate alignment of the second handle with an opening in the retractor blade;
wherein the plate engages a skin surface of a patient to resist said retraction by the soft tissue as second handle urges said blade to induce retraction.
According to a preferred embodiment the guide includes a first end which co operates with the first end of the first handle and a second end which receives a distal end of the second handle thereby guiding the second handle into engagement with said retractor blade.

In another broad form of a method aspect the present invention comprises: a method for retracting soft tissue in a surgical would during spinal surgery using an assembly comprising;
a retractor blade having a first distal end and a second end which engages a support member;
and an adjustable stop which engages a pressure plate which co operates with the retractor blade during retraction by applying pressure to the body of a patient,
the method comprising the steps of;
taking the retractor blade and attaching it to the support member;
inserting the retractor blade into a surgical incision;
adjusting a clamping assembly which co operates with a retaining member to exert a retraction force on the retractor blade;
allowing a bearing member to engage a skin surface of a patient;
manipulating the support member to induce retraction of the soft tissue against a bearing force applied by the bearing member opposite to the direction of retraction.

The method according to one embodiment comprises the further step of inserting the retaining member into a sleeve in the support member prior to engagement with the retractor blade and prior to insertion of the retractor into the incision.

In another broad form the present invention comprises:
an assembly for retracting soft tissue in a surgical wound, the assembly comprising;
a retractor blade having a first distal end comprising a blade arm and a proximal end;
a retaining arm and a clamping assembly which engages the retaining arm having a first end which is slidably retained by said retention arm and a second end which receives and retains a pressure plate assembly; the clamping assembly including means to enable vertical adjustment to alter the vertical position of the plate assembly relative to the retaining arm.

In another broad form the present invention comprises:
an assembly for retracting soft tissue in a surgical wound, the assembly comprising;
a retractor blade having a first distal end comprising a blade arm and a proximal end comprising a retaining arm; a clamping assembly which engages the retaining arm having a first end which is slidably retained by said retention arm and a second end which receives and retains a pressure plate assembly; the clamping assembly including means to enable fine clamping adjustment of the pressure plate when the clamping assembly is set in a selected location along the retaining arm; the fine adjustment determining the extent of clamping force exerted between the blade arm and the pressure plate.

According to a preferred embodiment, the clamping assembly is adjustable relative to the retention arm thereby enabling locking adjustment between the clamping assembly and the blade arm. Preferably, the clamping assembly is telescopically adjustable and includes openings which receive a locking pin which enable the clamping assembly to adopt various vertical positions. The plate assembly allows fine horizontal adjustment according to the clamping force required. The plate of said plate assembly engages a skin surface of a patient to provide an opposing force against retraction of soft tissue to maintain the desired retraction force.

In another broad form the present invention comprises:
an assembly for retracting soft tissue in a surgical wound, the assembly comprising;

a retractor blade having a first distal end comprising a blade arm and a proximal end comprising a retaining arm; a clamping assembly which engages the retaining arm having a first end which is slidably retained by said retention arm and a second end which receives and retains a pressure plate assembly; the clamping assembly including means to enable horizontal adjustment to selectively alter the distance between the blade arm and the clamping assembly.

The present invention provides an alternative to the known prior art and the shortcomings identified. The foregoing and other objects and advantages will appear from the description to follow. In the description reference is made to the accompanying representations, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying illustrations, like reference characters designate the same or similar parts throughout the several views. The following detailed description is, therefore, not to be taken in a limiting sense, and the scope of the present invention is best defined by the appended claims.

BRIEF DESCRIPTION OF DRAWINGS

FIG. 6 shows an elevation view of a retraction assembly according to an alternative embodiment;

FIG. 7 shows an end view of the retractor blade of FIG. 6;

FIG. 8 shows a top view of the retractor blade of FIG. 6;

FIG. 9 shows an opposite end view of the retractor blade of FIG. 6.

FIG. 10a shows a side elevation view of a retractor assembly according to an alternative embodiment.

FIG. 10b is an insert showing a perspective view of element 87 of FIG. 10 A.

FIG. 11a shows with corresponding numbering a cross sectional elevation view of the retractor assembly of FIG. 10a.

FIG. 11b shows the details with regard to locking rod 105.

FIG. 12 shows a top view of the connector engaging support member.

FIG. 13 shows the clamping member separated from retaining arm and rotated 90 degrees.

FIGS. 14a-e show various configurations of retractor blades.

FIG. 15 shows a schematic arrangement of a retractor assembly in use.

DETAILED DESCRIPTION

The examples referred to herein are illustrative and are not to be regarded as limiting the scope of the invention. While various embodiments of the invention have been described herein, it will be appreciated that these are capable of modification, and therefore the disclosures herein are not to be construed as limiting of the precise details set forth, but to avail such changes and alterations as fall within the purview of the description.

Figure 1:
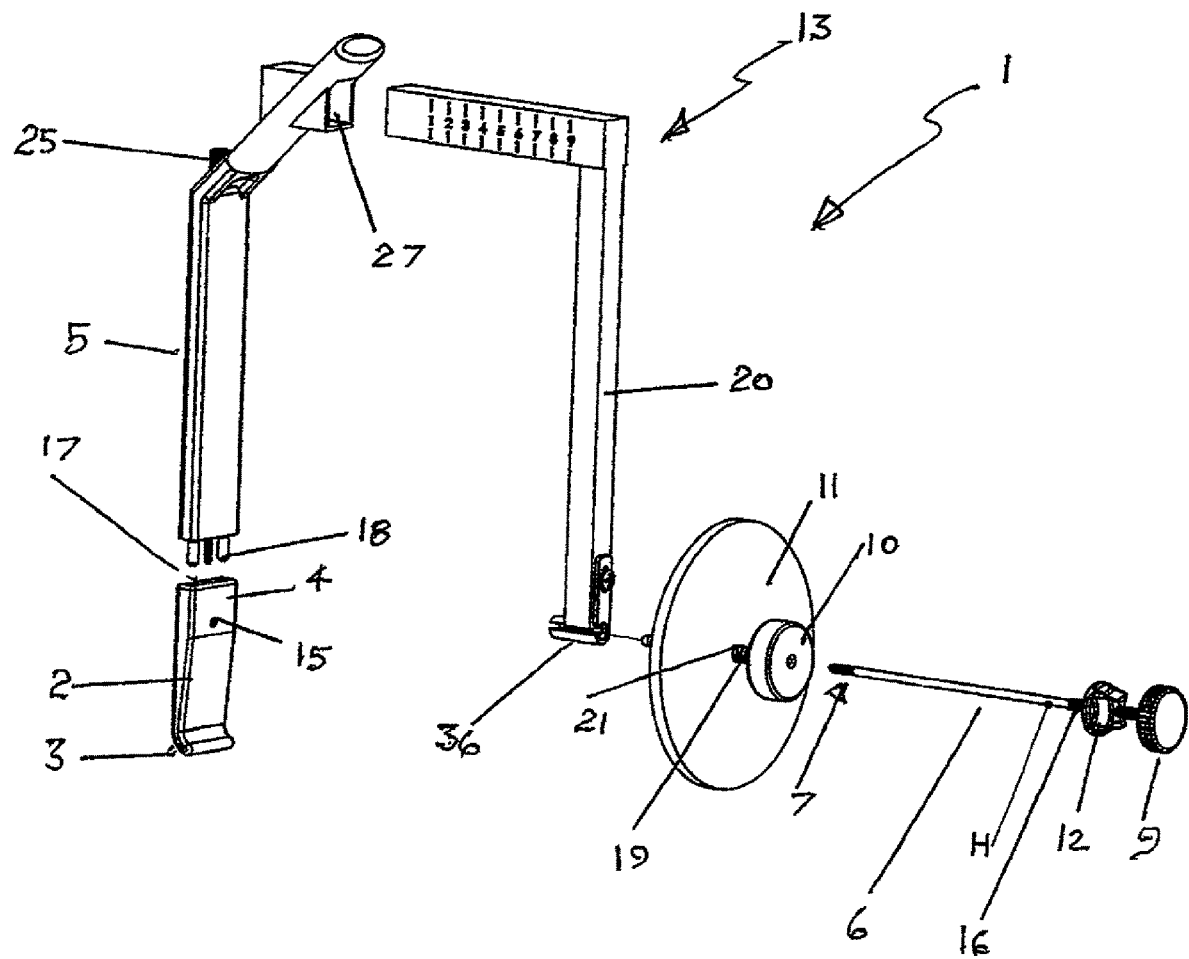
FIG. 1 shows a perspective view of a retraction assembly according to one embodiment.

FIG. 1 shows a perspective view of a retraction assembly 1 according to one embodiment. Assembly 1 for retracting soft tissue in a surgical wound comprises a retractor blade 2 having a first distal end 3 and a second end 4 which includes an associated handle 5. Assembly 1 further comprises a one piece trochar handle 6 having a pointed tip first end 7 which engages blade 2 and a second end 8 which includes a manual operating control element 9. Intermediate therebetween is adjustable stop 10 which engages a plate 11, wherein the plate engages a skin surface of a patient to resist retraction by the soft tissue. Trochar 6 also includes a locking nut 12 which co operates with thread 16 and enables locking of the plate 11 in a particular position for a predetermined extent of retraction. A washer which is not threaded can be employed as an alternative to plate 11. Retractor blade 2 has at its proximal end 4 a female recess 17 which receives male profile parts 18 which prevent rotation of blade 2. External retractor handle 5 has threaded bolt 25 that secures handle 5 to top surface recess 17 of blade 2. Square recess 27 to receives guide 13. Handle guide assembly 13 receives via end 36 sleeve 19, trocar or handle 6.

Figure 2:
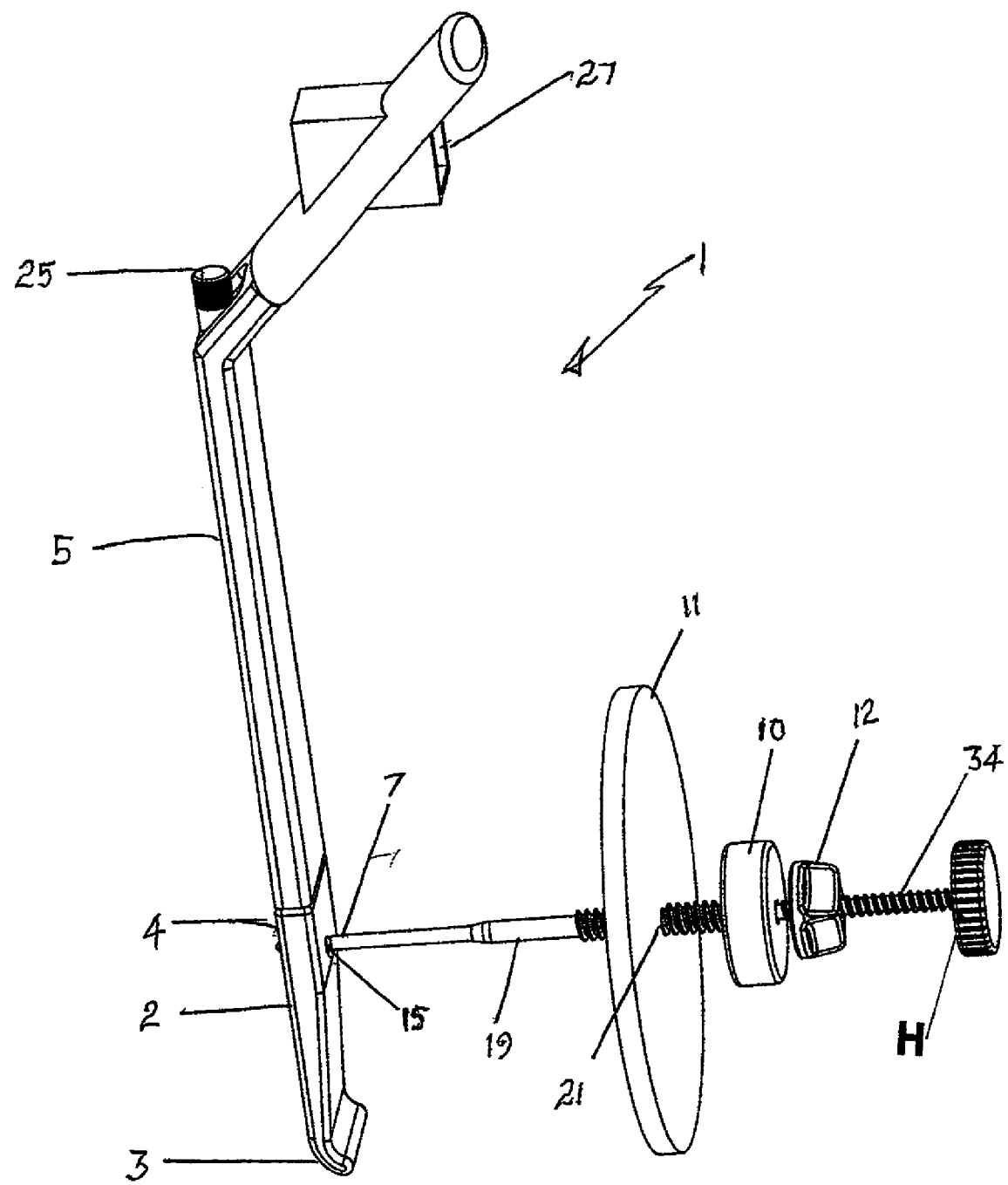
FIG. 2 shows with corresponding numbering a perspective view of the assembly of FIG. 1 including a guide member with trochar.

FIG. 2 shows with corresponding numbering a perspective view of the assembly of FIG. 1 Handle 5 includes a formation 27 which co operates with a guide member 13 (see FIG. 1). The formation 27 is an opening which receives an end of the guide member 13. According to one embodiment the second handle trochar 6 in FIG. 1 is replaced by an alternative handle H which includes at least one threaded region 34 which co operates with plate 11, adjustable stop and a locking nut 12. The guide member 13 co operates with the first handle 5 to enable setting of a retraction state. The assembly 1 allows adjustment of retraction by increasing or decreasing a retraction force. Plate 11 is preferably threaded for sleeve 19.

Typically a surgical wound is opened to expose or partially expose the surgical target. Structures and soft tissues to be retracted are identified. Retractor blade 2 of assembly 1 as shown in FIG. 1 is attached to a handle 5 and is inserted through an open wound and positioned. Threaded trocar 6 is passed through the wall of a patient's body through a separate wound along a line of a preferred line of retraction force to be established. The trocar 6 is then screwed into retractor blade 2 with end 7 penetrating opening 15. Pulling this trocar 6 applies the correct line of retraction force and thus acts as a second handle. Although a retraction force may be applied continuously by pulling with the hand, the retractor 5 can be stabilized at a desired position by turning nut 12 with washer on proximal part of trocar 6 until stop plate 11 contacts skin. Washer and nut 12 resists tissue pull on the handle by pressure on the external body wall. Handle 1 may be removed from blade 5 or left attached to help further adjustment. Turning nut 12 can adjust retractor blade 5.

A more complex arrangement is also envisaged, and described below using separate trocar 6 with sheath, and guide system 13. As can be seen in FIG. 1 trochar locates in sheath 19. This employs some of the following additional elements:

4. Method and apparatus for precise positioning of the trocar 6 so that it aligns with ideal blade position. I.e. Guide.

5. Large plate 11 and nut 12 are replaced with other mechanisms that spread muscle force over body wall. Such mechanism includes a separate plate that a sleeve engages via threads as shown in FIG. 1. Both envisaged embodiments of plate and washer variants increase surface area and are shaped to reduce chances of skin injury.

6. Sleeves which pass through body wall may also be employed with trocar 6. Purpose of the sleeve a. By having increased width of sleeve over trocar 6, this increases resistance to motion in line of body wall and thus provides a more stable position for the handle.

b. Such a sleeve 19 may also be attached to plate 11 thereby making plate 11 more stable.

c. By fixation to plate 11, sleeve 19 transmits forces from handle 6 to plate by presence of large collar 10 which engages nut 12 on handle 6.

d. Such a sleeve 19 allows trocar 6 to be removed and replaced with a threaded handle. This avoids having unguarded threads passing through body wall.

e. Length of sleeve and trocar can be made so that adjusting nut 12 on trocar 6 or handle limits depth that trocar or handle can penetrate.

f. Sleeve 19 may be adjustable relative to plate 11 which controls depth of sleeve 19 within the body.

Figure 3:
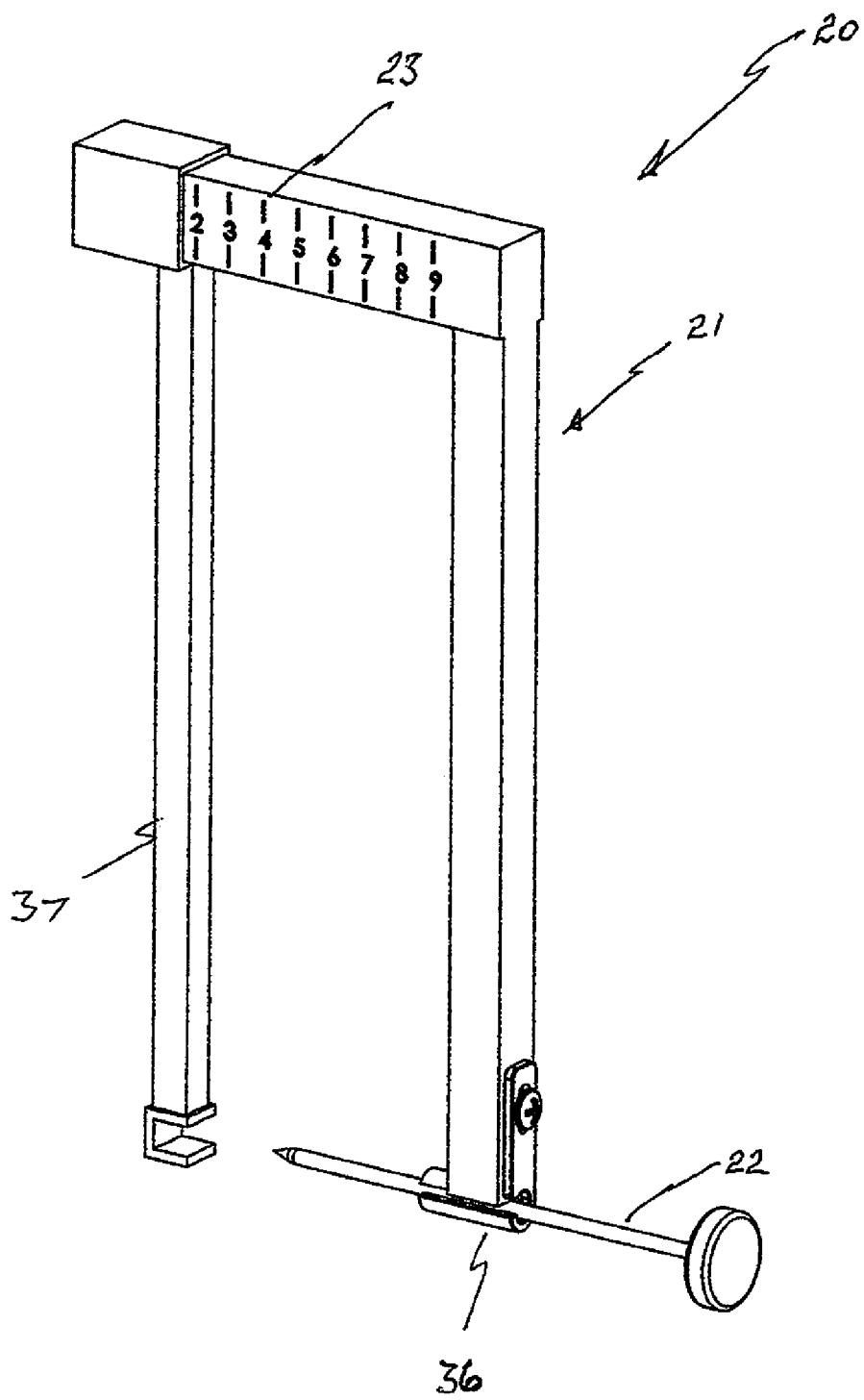
FIG. 3 shows an enlarged view of a guide assembly.

FIG. 3 shows an enlarged view of a guide assembly 20 isolated from the retraction assembly with trochar 22 engaged with end 36. Assembly acts as a positioning guide and comprises an adjustable frame 21 which acts externally as a guide and a safety stop for trocar 22 and sleeve (see FIG. 4). Guide assembly allows correct positioning internally of percutaneous handle 22 by indicating a finishing position and attitude/direction. Guide 20 is adjustable, with indicator 23 to indicate distance from external guide to a safety stop which can be used to set correct length of trocar and sleeve. External guide assembly 20 can be opened to allow removal of guide 20 once trocar 22 and sleeve (not shown) is positioned. FIG. 3 shows frame 20 engages with adjustable member 37. Member 37 engages frame member 21 via sleeve 38 which allows member 21 to slide relative to member 37. This allows the setting of a predetermined distance between the member 21 and member 37 so the surgeon is able to determine the distance of penetration of handle 22 into a second surgical wound to engage retractor blade 2 (see FIGS. 1 and 2).

Figure 4:
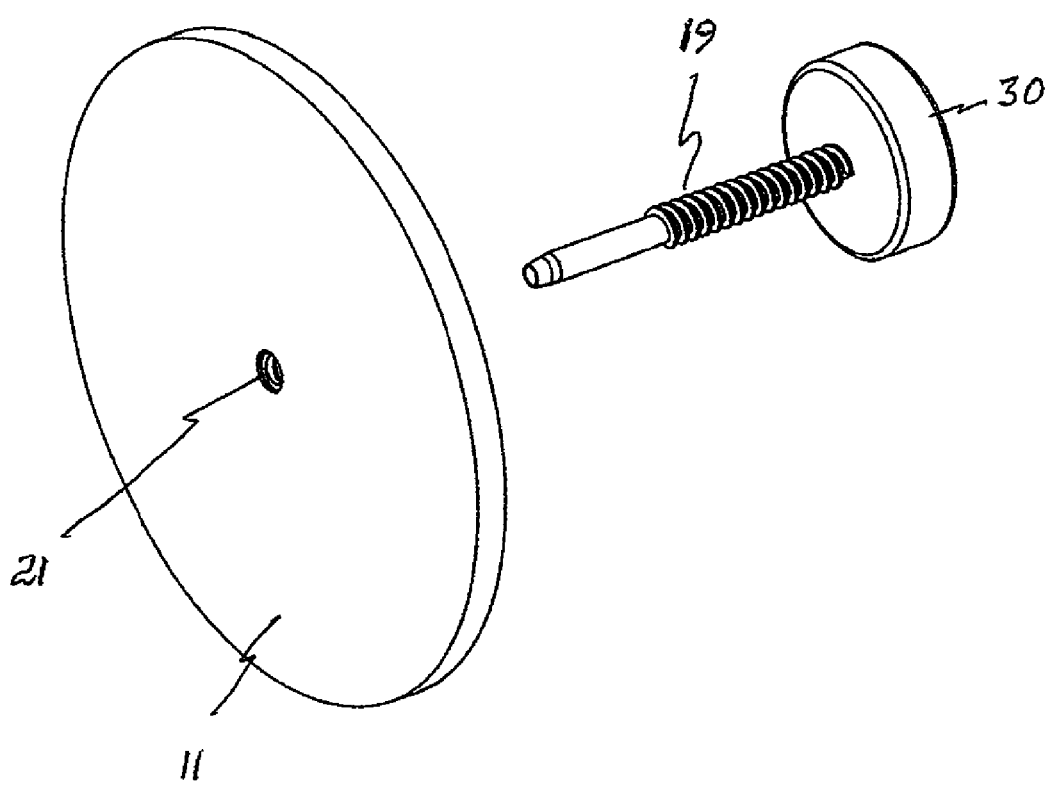
FIG. 4 shows an enlarged view of the plate and sleeve of FIG. 2.

FIG. 4 shows an enlarged exploded view of the plate 11 and sleeve 19 of FIG. 1. Plate 11 acts as an external Counter force plate and it will be appreciated that although the shape appearing in FIGS. 1 and 2 is annular other suitable shapes can be employed. Also a space frame or other contoured shape can be used as long as load is distributed evenly against the patient body wall without injuring skin and to provide maximum stability. A disc could be used with a threaded opening for sleeve 19 and may include an additional washer. Sleeve 19 is preferably a threaded tube that screws through plate 11 to desired depth as referenced from guide 20 (see FIG. 3). Sleeve 19 fits very tightly around trocar 6 of FIG. 1. Sleeve 19 has a large proximal collar 30 to acts as depth stop for handle 6. Sleeve 19 is connected to plate 11 and then inserted through body wall with trocar 6 until plate 11 engages the body wall. Sleeve 19 portion locates inside muscle and fat provide some stability. Amount of Sleeve protruding from plate 11 is set to have minimal overlap over psoas muscle to avoid restricting movement of the percutaneous handle.

Figure 5:
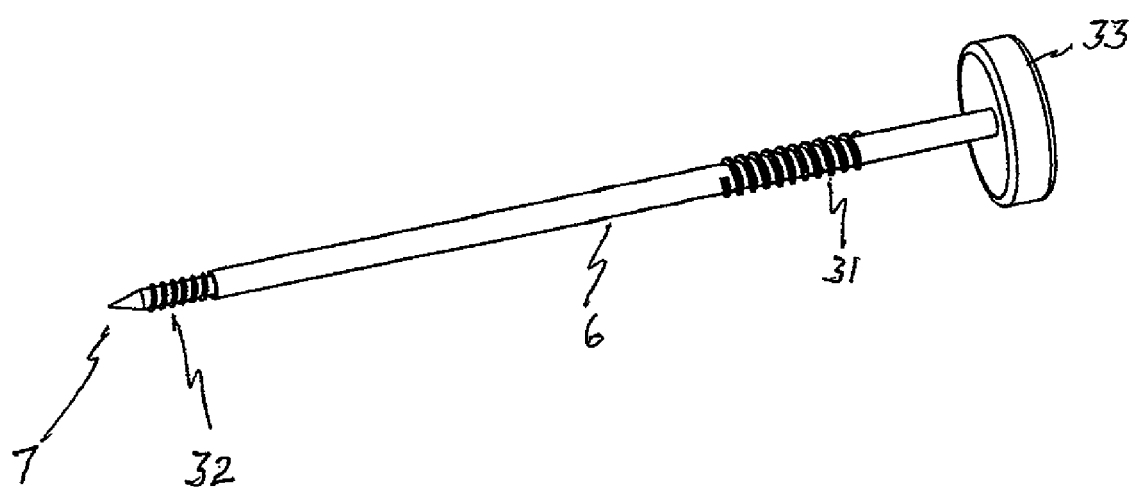
FIG. 5 shows the handle in isolation from the assembly of FIG. 2.

FIG. 5 shows the trochar handle 6 in isolation from the assembly of FIG. 1. Trocar 6 has a sharp pointed end 7 sharp pointed passes through sleeve 19 (see FIG. 1) so that sleeve 19 is replaced with percutaneous handle 6. Handle 6 includes a proximal thread 31 for adjustable nut 14 or made so only slightly longer than sleeve 19 to prevent over penetration and distal end thread 32 to engage blade 2 via opening 15. Handle 6 is inserted through body wall of a patient and guided by positioning guide 20 with sleeve 19 around it. Sleeve 19 is attached to counterforce plate 11. The percutaneous handle 6 slides in sleeve 19 and has a proximal knob 33 to enable pulling and to prevent rotation when nut 12 is turned. This handle 6 is threaded distally (32) to engage blade 2 and threaded proximally (31) for large adjusting nut 12 to engage against collar 30 of sleeve 19. As handle 6 is pulled muscle internally is retracted, large nut is spun on handle until it engages plate which thus by counterforce on body wall secures handle in position. More or less retraction is created by turning or releasing nut 12. Once percutaneous handle 6 is attached to threaded opening 15 of blade 2, initial open handle 5 can be retained to provide better and more controlled guidance but once correctly positioned and secured by tension against counter plate, open handle 5 may be removed. Handle 5 may be reattached as required.

The following describes how the assembly is used while adopting the guide 13. After wound opening, a guide 13 is positioned both internal and external to the wound. The external guide 13 sits against the skin aligning with internal guide 20 (see FIG. 2) which is positioned internally at desired position of the end of the sleeve 19. This position should also match with desired position for the perc handle. Measurements are read from guide 13 and using this as reference, sleeve 19 is now rotated in threaded opening 21 portion of plate 11 so that sleeve moves in or out relative to plate 11. Trocar 6 is inserted into sleeve 19 (with attached plate 11) and trocar 6 and sleeve 19 are then inserted through opening 22 of external guide 13, through the skin towards target. Once plate 11 is close to guide member 20, trocar 6 and sleeve 19 should be well engaged in tissues and preferably visible internally. External guide 13 is now opened to permit removal of guide from around sleeve 19. Sleeve 19 and trocar 6 are then advanced further until plate 11 engages skin and trocar 6 and needle are visible internally. The trocar 6 is withdrawn and a threaded handle with its proximal nut is passed through the sleeve 19 and attached to retractor blade 5. Pulling this handle pulls retractor blade 2 in the correct line of retraction force. This is handle number two. Although a retraction force may be continued using hand pressure the retractor 5 can be stabilized by attaching to plate 11 pressing over a large area of posterior body wall. Handle 1 may then be removed or left as desired.

Alternative Embodiments

22. Instead of separate trocar and percutaneous handle 6, these pieces could be Integrated into a 1 piece Trocar/handle which is threaded distally to engage with internal blade 2 and proximally for its own nut 12 to engage large washer. This embodiment avoids the use of a sleeve 19. A washer may have slot, so that drops over handle 6 after skin insertion, the nut on handle engaging the washer directly 23. Instead of threaded nut, rack and pinion or other mechanisms may be used to apply controlled forces between percutaneous handle and sleeve collar.
24. Trocar or percutaneous handle instead of engaging blade may also engage with handle 5
25. Various mechanism e.g. key mechanism, split pins, various axle fittings etc may be used to connect percutaneous handles and blade. The Method of engagement may be varied to suit requirements of handle e.g. if handle is needed to steer blade other than simply by pulling, a larger handle maybe inserted through a larger wound via a series of concentric tubes dilating a channel through which handle is passed.
26. Blades can be any shape or size to suit local anatomy or amount of retraction required.
27. Blades of different shape are interchangeable
28. Blades have cone shaped opening to allow easy positioning and engagement of threaded part of handle.
29. Sleeve and plate could be one piece with set depth for sleeve
30. It is also envisaged that a targeting guide can be employed instead of having an external guide that opens and closes around handle as shown. External arm is reversibly fixed to plate. Sleeve is separate from plate. Thus a hole in the plate determines a correct alignment. Measurements are taken from a frame about sleeve depth. Frame is unlocked. Sleeve is screwed to correct depth which will push the plate away from the body wall. Trocar and sleeve are inserted through body wall until plate is flush with skin. Targeting guide is then removed. Various variations of elements are possible all with same broad intent and principles of action.
31. Guide function may be accomplished by incorporation of sleeve and plate as part of external guide
32. Varying the angle of percutaneous handle thru body wall may also impart downward or upwards force on retractor blade when pulled which helps direct force of blade as desired.
33. It is also envisaged that a percutaneous handle could be used to support an internal frame or mechanism that in turn supports multiple retractor blades for e.g. a transpsoas approach.
34. Internal frames supporting several blades may also be supported by percutaneous handle e.g. peritoneal blade clip on like an odontoid frame. A frame incorporating round bars in order that blades might rotate is envisaged. Blades might be fixed or hinge about sides of such frames.
35. Internal part of the guide may incorporate handle 1 as shown in FIG. 5
36. A series of dilators may be passed over trocar 6 to create protected passage for insertion of various handles that include hooks or keying mechanisms for non threaded engagement with blades.
37. Methododology. It is envisaged that handle is passed not only from outside through skin and into wound but also from wound out of skin, in which case handles and blades and other parts are attached after tunneling.
38. Handles may be straight or curved with bosses and variations of width with tapers to accommodate external threads and other mechanisms to engage blades and other parts.
39. Retractor blades individual may be round or tubular in various shapes.
40. Retractor blades may be individual or as part of Multi-bladed retractors inserted individually or as part of assembly that allows movements of blades. In this embodiment percutaneous handle or handles attaches to some part of assembly adding to stability or ability to control.
41. Multiple percutaneous handles may be employed.
42. Percutaneous handle may be similar to threaded Steinman pin, inserted with power or hand driver. After insertion, insertion handle or driver may be removed and detachable handle added with nuts and washers for manual control and final positioning Alternative Embodiment FIG. 6 shows an elevation view of a retraction assembly 50 according to an alternative embodiment. Assembly 50 according to the embodiment shown is used for retracting soft tissue in a surgical wound and comprises a retractor blade 51 having a distal end 52 and a proximal end 53. Distal end 52 includes a formation 54 which locates inside a patient wound. FIG. 7 shows with corresponding numbering an end view of the retractor blade 51 of FIG. 6. Retractor blade 51 has a blade arm 55 which terminates in distal end 52. Retaining arm 56 terminates in proximal end 53 and includes openings 57 which allow incremental adjustment and braking of clamp assembly 58 and finger opening 59 which allows an operator to pull back on retaining arm 56 to urge blade arm 55 in the direction of pull. This also allows movement of blade 51 relative to clamp assembly 58. This assists in setting different retraction states and forces applied to soft tissue depending upon the surgical patient requirements.

FIG. 8 shows a top view of the retractor blade of FIG. 6. Although blade 51 is shown with blade arm 55 disposed normally to retaining arm 56, that angle can be varied according to design requirements and particular applications and orientations of blade arm 55 required. Clamp assembly 58 is shown engaged to retaining arm 56 via depending arm 60. Clamp assembly further comprises adjustable support arm 61. Support arm 61 has a recess 62 which receives and retains arm 60. Wheel 62 allows adjustment of support arm 61 relative to depending arm 60. Recess 62 allows travel of arm 61 relative to depending arm 60 thereby enabling the adjustment of the distance indicated by H between retaining arm 56 and shaft 63 of adjustment handle assembly 64. Arm 60 includes openings 65 which allow selective adjustment of locking pin 66 so that height H can be adjusted by moving support arm 61 up or down. Support arm 61 has at its distal end 67 an opening 68 which receives and retains shaft 63. End 69 of shaft 63 engages pressure plate 70 which includes outer surface 71 which in use engages the skin of a patient. End 69 as shown is contoured to enable relative movement between plate 70 and shaft 63. This allows the attitude of surface 71 of plate 70 to adjust to contours of a patient. Plate 70 can rotate about an axis through shaft 63 and can also tilt relative to that axis.

FIG. 9 shows an opposite end view of the retractor blade retaining arm 56 as it engages depending arm 60. Arm 60 includes recess 72 which receives therein retaining arm 56. In use depending arm 60 is capable of movement relative to retaining arm 56 thereby enabling adjustment of the distance between blade arm 55 and surface 71 of plate 70. Distance I between blade arm 55 and surface 71 of plate 70 is adjustable depending upon the patient. Adjustment handle 64 urges shaft 63 and plate 70 in the direction of the patient or away from the patient. The plate 70 engages a skin surface of a patient to resist retraction forces applied to the soft tissue. Shaft 63 is according to one embodiment adapted with a threaded connection which engages distal end of the support arm 61. Turning handle 73 increases or decreases as required the gripping force between surface 71 when in engagement with skin of a patient and the blade arm 55. Since depending arm 60 can be moved and repositioned along retaining arm 56, this in addition to the adjustments enabled by adjustment handle assembly 64 accommodates different distances between the blade arm 55 and plate 70. Also since clamp assembly 58 allows adjustment of distance H the assembly 50 has wide scope of both vertical and horizontal adjustment to accommodate patient differences. Typically a surgical wound is opened to expose or partially expose the surgical field. Structures and soft tissues to be retracted are identified. Retractor blade arm 55 of assembly 50 as shown in FIG. 6 is inserted through an open wound and positioned. Either before or after this clamp assembly 58 is attached and adjusted vertically and horizontally as indicated above. Pulling on opening 59 initially manually applies the required retraction force which is then locked into position and stabilised by urging plate 70 into engagement with the patient's skin.

FIG. 10 shows a side elevation view of a retractor assembly 80 according to an alternative embodiment. Assembly 80 comprises a first supporting member 81 having a first end 82 and second end 83. First end 82 engages an adjusting assembly 84 which comprises a connecting assembly 85. Second end 83 engages a connector 86 which retains a retractor blade 87. Depending from connecting assembly 85 is retaining arm 88 which retains a height adjustable clamping member 89. Clamping member 89 is capable of movement relative to retaining arm 88 and comprises a first end 90 terminating in a bearing face 91 which opposes retractor blade 87 and a second end 92 which includes an actuating member 93 which enables selective adjustment of the position of clamping member 89 relative to retaining arm 88. Connecting assembly 85 includes a runner 94 which travels along support member 81. Retaining arm 88 engages runner 94 via end 95. Runner 94 further comprises an actuator 96 which engages support member 81 and contributes to retention of runner 94 in a position selected by a user of the retractor assembly 80. Actuator 96 is pivotally attached to runner 94 by abutments 97 and 98. Locking knob 99 retains runner 94 against first support member 81 and allows adjustment of the runner 94 relative to supporting member 81. This allows a user to selectively adjust a distance between bearing face 91 and retractor blade 87. Support member 81 further comprises an array of teeth 100 which allows incremental adjustment of connection assembly 85 along support member 81. Actuator 96 engages corrugations or teeth on a surface of support member 81. In this case, teeth array 100 is shown on the top of member 81. Actuator 96 can be arranged to engage teeth on one or more surfaces. Formations 116 are able to be engaged by actuator 96 to effect incremental adjustment of runner 94. Alternative formations can be used to effect the incremental adjustment.

FIG. 11 shows with corresponding numbering a cross sectional elevation view of the retractor assembly 80 of FIG. 10. Retractor blade 87 engages connector 86 via end 101. Retractor blade 87 is fed into a slot 102 located in connector 86. Clamping member 89 is selectively retained along retention arm 88 via a series of recesses 117 via locking rod 105. Locking rod 105 including leading end 106 which engages recess 104 to select the position of clamping member 89. Actuating member 93 allows locking rod 105 to be selectively withdrawn from recess 104 and repositioned as required. Rod 105 is biased to a locking position via spring 107 which urges rod 105 into engagement with recess 104. To release and move clamping member 89 requires the user to pull actuating member 93 against biasing spring 107. Retaining arm 88 is retained at end 109 at end 95 of by connection assembly 85 via locking screw 110. Release of locking screw 110 allows arm 88 to be released from runner 94 connection assembly 85.

FIG. 12 shows a top view of the connector 86 engaging support member 81. Connector 86 retains retractor blade 87 (see FIG. 10) via slot 102 which and retains support member 81 via locking pin 103 which engages end 83. Teeth array 100 can be seen on the top surface of support member 81.

FIG. 13 shows the clamping member 89 separated from retaining arm 88 and rotated 90 degrees. From this view opening 111 which retains arm 88 can be seen. The retractor assembly 80 can be incrementally adjusted both vertically in the direction of arrow 112 and horizontally in the direction of arrow 113. This allows the assembly to be adjusted to suit retraction geometry for each particular patient.

FIGS. 14*a-e* show various configurations of retractor blades 130, 131, 132, 133 and 134 which can be detachable removed from the retractor assembly 80. Blade 130 has a distal end 135 which terminates in an engaging point 136 and a proximal end 137 which connects to retraction assembly 80. Similarly blades 131, 132, 133 and 134 have respective ends 138, 139, 140 and 141 which engage retractor assembly 80. It will be appreciated by persons skilled in the art that there are many retractor blade configurations which can be connected to the retractor assembly 80 (See FIGS. 10 and 11). In each case the selection of retractor blade size, length, curvature or geometry can be determined by the surgical requirements and/or patient anatomy.

FIG. 15 shows a schematic arrangement of a retractor assembly 150 in use. Assembly 150 comprises a first supporting member 151 having a first end 152 and second end 153. First end 152 engages an adjusting assembly 154 which comprises a connecting assembly 155. Second end 153 engages a connector 156 which retains a retractor blade 157. Depending from connecting assembly 155 is retaining arm 158 which retains a height adjustable clamping member 159. Clamping member 159 is capable of movement relative to retaining arm 158 and comprises a first end 160 terminating in a bearing face 161 which opposes the patient body and retractor blade 157 and a second end 162 which includes an actuating member 163 which enables selective adjustment of the position of clamping member 159 relative to retaining arm 157. Connecting assembly 155 includes a runner 164 which travels along support member 151. Retaining arm 158 engages runner 164 via end 165. Runner 164 further comprises an actuator 166 which engages support member 151 and contributes to retention of runner 164 in a position selected by a user of the retractor assembly 150. Actuator 166 is pivotally attached to runner 164 by abutments 167 and 168. Locking screw 169 retains runner 164 against first support member 151 and allows fine adjustment of the runner 164 relative to supporting member 151. This allows a user to selectively adjust a distance d between bearing face 161 and retractor blade 157. The retractor blade 157 resists a force applied to the skin 170 of a patient. Bearing face 161 applies pressure to bearing member 171. Bearing member 171 can be a plate or softer pliable or elastic material which can gently transmit compression to the skin.

Bearing plate 161 or bearing member 171 could be considerably larger and various shapes to spread clamping force across larger body surface area to accommodate particular anatomical requirements e.g. in cervical surgery.

Figure 16:
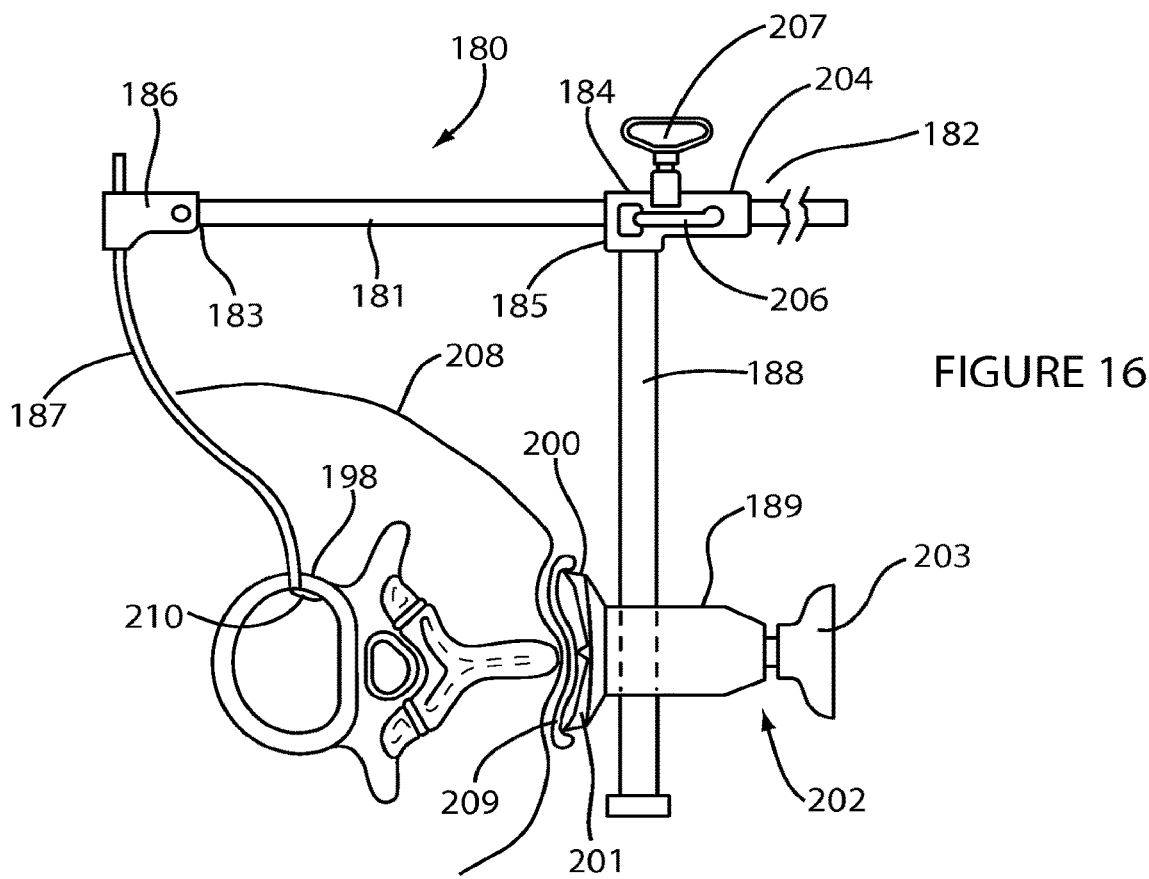
FIG. 16 shows a cross sectional elevation of a clamping retractor assembly showing a tooth of a retractor blade engaging an annulus.
Figure 18:
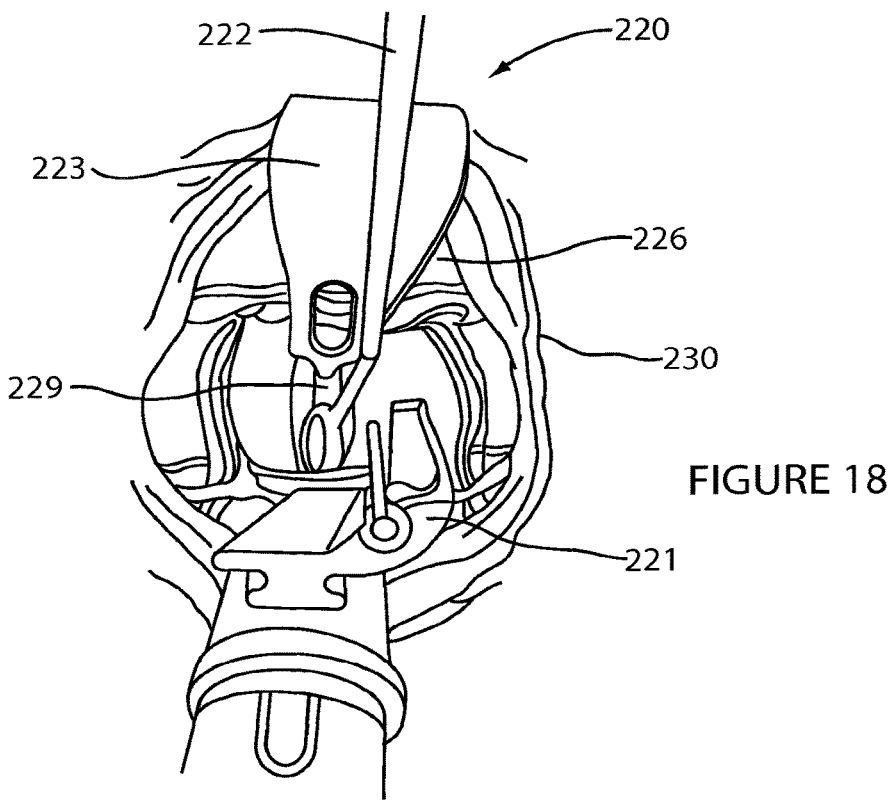
FIG. 18 shows a surgical incision in the skin of a patient with a G Clamp according to the invention and used in conjunction with another retractor and offset tool.
Figure 19:
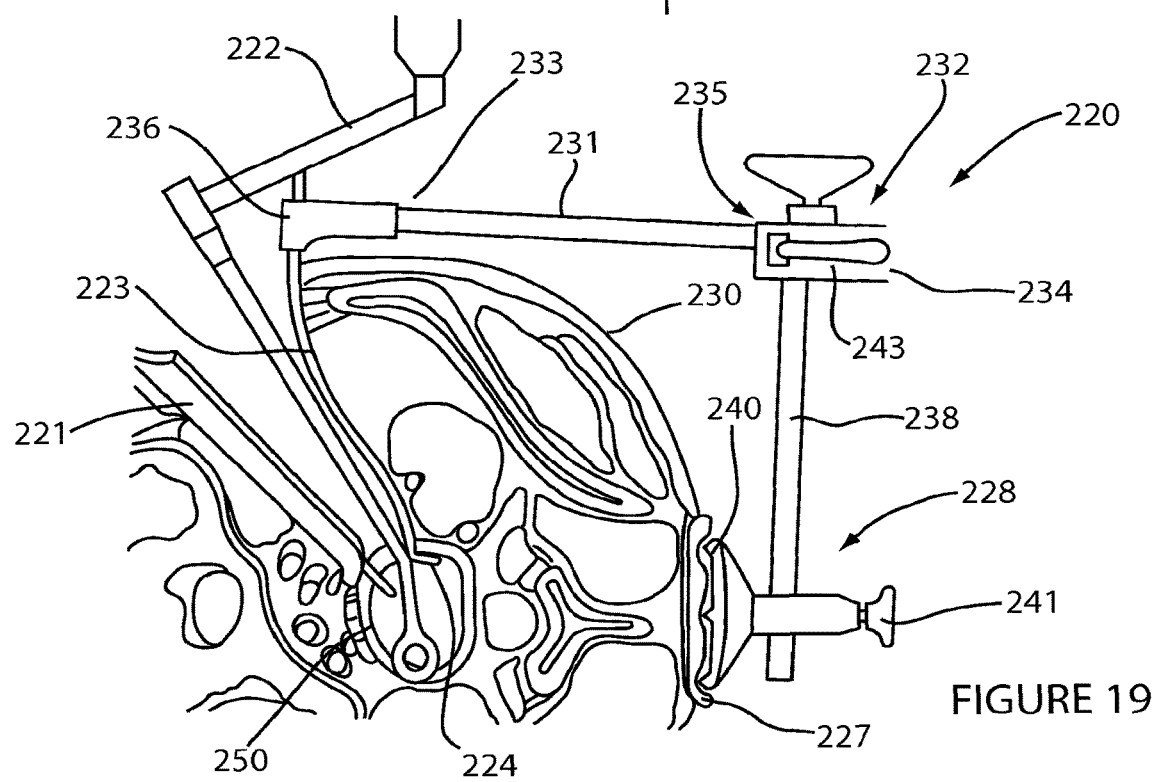
FIG. 19 shows a cross sectional elevation of the arrangement of FIG. 18 showing a reverse tooth of a retractor blade engaging an annulus.

FIG. 16 shows a cross sectional elevation of a clamping retractor assembly 180 showing a tooth 210 of blade 187 engaging an annulus 198. Assembly 180 comprises a supporting member 181 having a first end 182 and second end 183. First end 182 engages an adjusting assembly 184 which comprises a connecting assembly 185. Second end 183 engages a connector 186 which retains a retractor blade 187. Depending from connecting assembly 185 is retaining arm 188 which retains a height adjustable clamping member 189. Clamping member 189 is capable of movement relative to retaining arm 188 and comprises a first end 200 terminating in a bearing face 201 which opposes the patient body and retractor blade 187 and a second end 202 which includes an actuating member 203 which enables selective adjustment of the position of clamping member 189 relative to retaining arm 187. Connecting assembly 185 includes a runner 204 which travels along support member 181. Retaining arm 188 engages runner 204. Runner 204 further comprises an actuator 206 which engages support member 181 and contributes to retention of runner 204 in a position selected by a user of the retractor assembly 180. Locking screw 207 retains runner 204 against first support member 181 and allows adjustment of the runner 204 relative to supporting member 181. The retractor blade 187 resists a force applied to the skin 208 of a patient. Bearing face 201 applies pressure to bearing member 209. Bearing member 209 can be a plate or softer pliable or elastic material which can gently transmit compression to the skin 208. Retracting blade 187 is curved towards annulus 198. This geometry increases retraction efficiency and allows the blade 187 and clamp 189 to co operate to balance forces generated for retraction stabilising the retraction assembly G clamp. Tooth 210 of blade 187 fits into a cut disc space. As the G Clamp blade 187 retracts, the tooth 210 inside the disc space prevents the blade from lateral motions (i.e. relative to a longitudinal axis of the disc) and prevents it from lifting up. Since the blade is in the cut disc space the cut disc annulus limits and prevents the blade from going too far backwards and over compressing the tissues. The surgeon is thus able to define how far the retractor will move backwards by cutting the annulus posteriorly to the desired posterior limit. The ability to limit and set the amount of posterior motion by using the cut annulus 198 (which is a tough structure), is a useful advantage for the surgeon and is enabled by the G clamp. Retraction can be wound back or wound up using the ratchet mechanism described earlier but using the cut annulus 198 allows prevention of over compression of tissues. The reverse angled distal tooth 210 included in blade 187 allows improved surgical method for retraction. Blade 187 with its reverse angled distal tooth 210 requires a cut to be made in the annulus 198, the posterior limit of which is determined by the surgeon. The distal end of the tooth 210 is engaged into the disc either directly into the cut annulus 198 or immediately under the cut annulus as shown in FIG. 15. In use after retracting the blade 157 the posterior limit of blade retraction is limited by the proximal section of tooth 188, engaging posterior limit of the cut in the annulus. The section of distal tooth lying horizontally beneath the posterior limit of the cut prevents the blade by lifting up or laterally out of the disc space. This provides increased stability for the retractor blade 187. One purpose and advantage of the apparatuses as illustrated in a surgical context is to avoid excessive retraction of the psoas muscle and potential injury of the lumbar nerves contained within this muscle. This method of limiting the amount of retraction by cutting the patient's vertebral disc is enabled in this case by inserting a tooth 210 of blade 187 to limit lift retractor blade out. is novel, as is its application using the assembly shown in FIG. 15. This method and instrumentation has particular value in an oblique or anterior to psoas approach to the spine. The assembly shown in use in FIGS. 15,16, and 17 (below) is particularly useful in an anterior to psoas approach to the lumbar spine. In this approach retraction of psoas by the assembly shown in FIG. 15, allows disc access by offset instruments to allow an orthogonal approach to the disc space (particularly L45 and L5/s1 disc spaces) which is desirable. Bony or soft tissue anatomy would otherwise prevent being truly orthogonal to the disc spaces essential for maximum safety in this surgery. Refer to FIGS. 18 and 19 below. With conventional systems the bony anatomy of the pelvis would prevent use of straight instruments being orthogonal to spine.

Figure 17:
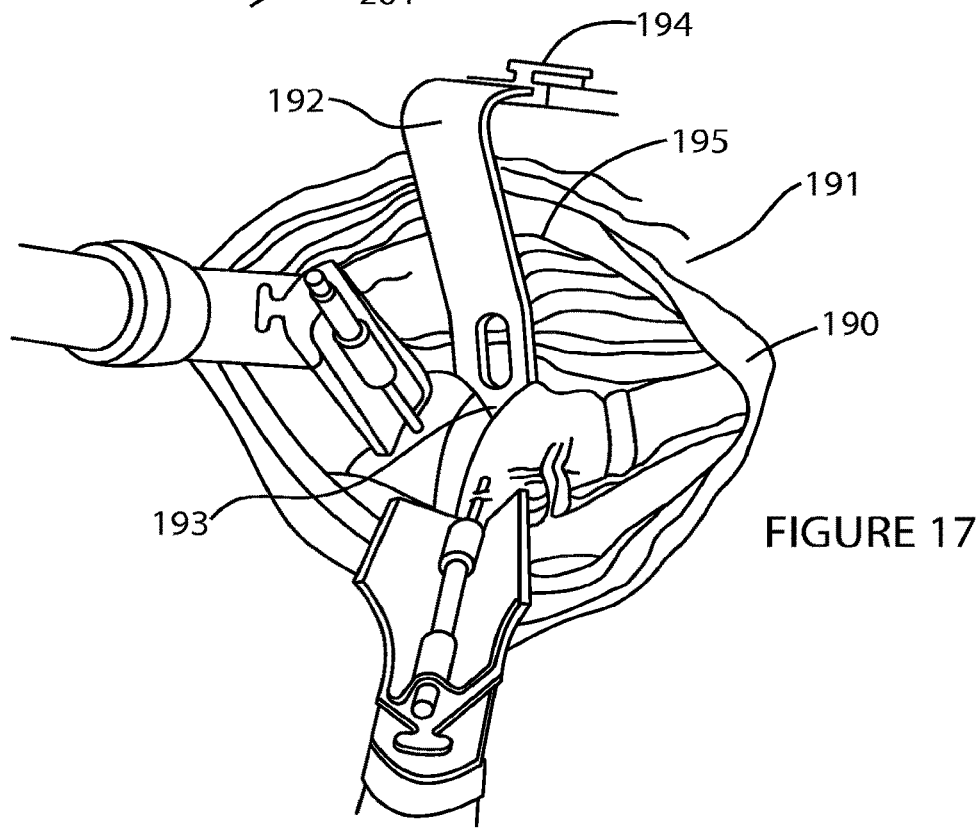
FIG. 17 shows a surgical incision in the skin of a patient with retractor blade in use.

FIG. 17 shows a surgical incision 190 in the skin 191 of a patient with retractor blade 192 showing blade 192 in use. Blade 192 has a distal end tooth 193 that curves backwards. (see also the blade 157 in FIG. 15). Blade 192 is retained by support member 194 which has the characteristics of the retractor assembly 150 as described in FIG. 15. Blade 192 retains tissues 195 and gains its purchase from a bearing plate (see FIG. 16).

FIG. 18 shows a surgical incision in the skin 230 of a patient with a G Clamp 220 according to the invention and used in conjunction with another retractor 221 and offset tool 222. Blade 223 has a distal end reverse tooth 224 that curves backwards. Blade 223 is retained by support member 225 which has similar operation and characteristics of the retractor assembly 150 as described in FIG. 15 so further detailed description of tis operation is not required. Blade 223 retains tissues 226 and gains its purchase from a bearing plate 227 (see FIG. 19) associated with clamping assembly 228. In this approach retraction of psoas by the assembly shown allows disc access by offset instrument 222 to allow an orthogonal approach to the disc space 229 (particularly L45 and L5/s1 disc spaces) which is desirable. Bony or soft tissue anatomy would otherwise prevent being truly orthogonal to the disc spaces essential for maximum safety in this surgery.

FIG. 19 shows a cross sectional elevation of the arrangement of G clamp 220 of FIG. 18 showing a reverse tooth 224 of retractor blade 223 engaging an annulus 250. Assembly 220 comprises a supporting member 231 having a first end 232 and second end 233. First end 232 engages an adjusting assembly 234 which comprises a connecting assembly 235. Second end 233 engages a connector 236 which retains retractor blade 223. Retaining arm 238 retains a height adjustable clamping member 239 which is capable of movement relative to retaining arm 238. Bearing face 240 opposes patient body 230 and retractor blade 223 and includes an actuating member 241 which enables selective adjustment of the position of clamping assembly 228 relative to retaining arm 238. A runner 243 which travels along support member 231 comprises an actuator 244 which engages support member 231 and contributes to retention of runner 243 in a position selected by a user of the retractor assembly 220. Tooth 224 of blade 223 fits into a cut disc space. As the G Clamp blade 223 retracts, the tooth 224 inside the disc space prevents the blade from lateral motions (i.e. relative to a longitudinal axis of the disc) and prevents it from lifting up. Since the blade is in the cut disc space the cut disc annulus limits and prevents the blade from going too far backwards and over compressing the tissues. The surgeon is thus able to define how far the retractor will move backwards by cutting the annulus 250 posteriorly to the desired posterior limit. Retraction can be wound back or wound up using the ratchet mechanism described earlier but using the cut annulus allows prevention of over compression of tissues.

Other Applications for Percutaneous Retractor Handle Technology

Another spinal operation, where retraction of muscles is difficult is for lumbar pedicle screw insertion. This is difficult because of the force required to get the correct line of entry for screw insertion tools from a conventional midline approach. Strong retraction is required and this has led to very strong devices which may easily injure muscles. Attempts to improve efficiency by using metal retractors which lever off the bone may injure the bone, facet joints or fracture the transverse process. A percutaneous handle would help stabilize and avoid such a need.

Another circumstance where retractor stability is an issue is when using tubular retractors inserted as a series of increasing size tubes. These often require table fixation to stabilize as direction of entry may be displace by tissue forces. Table mounting is often required to stabilize. A percutaneous handle would help stabilize and avoid such a need.

A further circumstance where retractor stability is an issue is when using multi bladed retractors that are inserted as part of an assembly and then inserted within the wound. Opening retractor may move retractor from desired position and often requires the addition of a table mounted arm. An alternate method of stabilizing will be to add percutaneous handle to a. Handle is stable in body wall but this stability can be further increased by addition of counterforce plate which may compress body wall against sides of retractor. Percutaneous handles may also be employed in other forms of surgery e.g. gynaecological or pelvic surgery where approach is via body cavity but application of retractor force would be helpful.

It will be recognized by persons skilled in the art that numerous variations and modifications may be made to the invention broadly described herein without departing from the overall spirit and scope of the invention.

What is claimed is:

1. A clamping retractor assembly for retracting soft tissue in a spinal surgery incision, the clamping retractor assembly comprising;
    a support member having first and second ends;
    a retractor blade having a blade arm, a distal end and a proximal end retained by the support member;
    a retaining arm co-operating with the support member, the support member receiving and supporting the co-operating retaining arm;
    a clamping member having a bearing face which opposes the retractor blade and which engages the co-operating retaining arm and allows the clamping member to move over a distance relative to the distal end of the retractor blade between a clamped state in which body tissues are subject to a clamping force induced by co-operation between the retractor blade and pressure applied on an outside surface of the body of a patient via the bearing face, thereby retracting a wall of an incision at least partially dependent upon the retraction force applied and an unclamped state in which the assembly does not induce a clamping force; and
    a runner which supports the retaining arm and comprises a locking member which allows locking of said runner at a selected position along the support member;
    wherein a vertical position of the clamping member is selectively adjustable via an actuating member, along the retaining arm and relative to the support member.

2. The assembly according to claim 1 wherein the runner is adjustable incrementally along the length of the support member.

3. The assembly according to claim 2 wherein the clamping member is capable of advancing to a clamping state and retracting to an unclamped state relative to the retractor blade responsive to travel of the runner along the support member.

4. The assembly according to claim 3 wherein the runner is incrementally adjustable along the length of the support member by co-operation between an actuator and formations.

5. The assembly according to claim 4 wherein the actuating member is spring biased to lock the clamping member against the retaining arm.

6. The assembly according to claim 5 wherein the locking member comprises a manually operable locking knob which locks the runner to the support member.

7. The assembly according to claim 6, wherein, a locking rod in the clamping member includes a pin which selectively engages spaced apart recesses in said retaining arm.

8. The assembly according to claim 7 wherein the retractor blade is releasable from the first end of the support member.

9. The assembly according to claim 8 wherein, the location of the runner along the support member is incrementally adjustable by co-operation between the formations and the actuator.

10. The assembly according to claim 1 wherein the retractor blade is angled in the direction of the clamping member and further comprises a distal end formation which arrests slippage of tissue about the blade.

11. The assembly according to claim 10 wherein the retractor blade is elastically deformable.

12. The assembly according to claim 11 wherein a retraction force is increased or decreased by selective adjustment of the position of the runner.

13. The assembly according to claim 12 wherein a retraction force is increased or decreased by selective adjustment of the position of the clamping member.

14. The assembly according to claim 13 wherein the bearing face provides an opposing force against retraction of soft tissue to maintain the desired retraction force through the retractor blade.

15. The assembly according to claim 14 wherein the retraction assembly is adjustable to allow the clamping member to travel in the direction of the support member and in a direction parallel to the support member.

* * * * *